(12) United States Patent
Hutchinson et al.

(10) Patent No.: US 8,202,226 B2
(45) Date of Patent: Jun. 19, 2012

(54) PROVIDING AUTOMATED OR MANUAL GUIDANCE ON DYNAMIC PATIENT POSITIONING BASED ON MEASURED VARIABLES FOR VENTILATION CONTROL

(75) Inventors: George Hutchinson, San Antonio, TX (US); Royce W. Johnson, Universal City, TX (US)

(73) Assignee: KCI Licensing, Inc., San Antonio, TX (US)

( * ) Notice: Subject to any disclaimer, the term of this patent is extended or adjusted under 35 U.S.C. 154(b) by 1190 days.

(21) Appl. No.: 12/016,030

(22) Filed: Jan. 17, 2008

(65) Prior Publication Data

US 2008/0202527 A1    Aug. 28, 2008

Related U.S. Application Data

(60) Provisional application No. 60/881,907, filed on Jan. 23, 2007.

(51) Int. Cl.
*A61B 5/08* (2006.01)
*G01N 33/48* (2006.01)

(52) U.S. Cl. ........... 600/529; 600/533; 600/534; 702/19
(58) Field of Classification Search .................. None
See application file for complete search history.

(56) References Cited

U.S. PATENT DOCUMENTS

| | | |
|---|---|---|
| 4,114,625 A | 9/1978 | Onat |
| 4,214,493 A | 7/1980 | Elhaus |
| 4,638,516 A | 1/1987 | Vrzalik |
| 4,730,606 A | 3/1988 | Leininger |
| 4,763,643 A | 8/1988 | Vrzalik |
| 4,868,937 A | 9/1989 | Connolly |
| 4,909,259 A | 3/1990 | Tehrani ........................ 128/718 |
| 4,947,496 A | 8/1990 | Connolly |
| 4,986,268 A | 1/1991 | Tehrani |
| 5,003,654 A | 4/1991 | Vrzalik |
| 5,006,106 A | 4/1991 | Angelchik |
| 5,142,719 A | 9/1992 | Vrzalik |
| 5,152,021 A | 10/1992 | Vrzalik |
| 5,299,334 A | 4/1994 | Gonzalez |
| 5,308,326 A | 5/1994 | Zimmon |

(Continued)

FOREIGN PATENT DOCUMENTS

EP    1 579 882 A1    9/2005

(Continued)

OTHER PUBLICATIONS

Bein et al. Effects of extreme lateral posture on hemodynamics and plasma atrial natriuretic peptide levels in critically ill patients. Intensive Care Medicine, vol. 22, 1996, pp. 651-655.*

(Continued)

*Primary Examiner* — Russell S Negin
(74) *Attorney, Agent, or Firm* — Fulbright & Jaworski L.L.P.

(57) ABSTRACT

Methods and systems that incorporate automated or manual control of ventilation and kinetic rotation therapy are provided. In one exemplary embodiment, an artificial ventilator is used to artificially ventilate one of the patient's lungs, the status of the artificially ventilated lung is determined by measuring one or more ventilation status measures, and one or more of the ventilation status measures is used to provide feedback for controlling the positioning of the patient. In some exemplary embodiments, the feedback is used for automated control of the positioning of the patient, while in other exemplary embodiments, the feedback is used as guidance for manual control of the positioning of the patient.

27 Claims, 9 Drawing Sheets

U.S. PATENT DOCUMENTS

| | | | |
|---|---|---|---|
| 5,314,573 A | 5/1994 | Higuchi et al. | |
| 5,398,692 A | 3/1995 | Hickey | |
| 5,603,133 A | 2/1997 | Vrzalik | |
| 5,660,170 A | 8/1997 | Rajan et al. | 128/204.18 |
| 5,802,645 A | 9/1998 | Vrzalik | |
| 5,819,723 A | 10/1998 | Joseph | |
| 5,975,077 A | 11/1999 | Hofstetter et al. | 128/204.24 |
| 6,086,558 A | 7/2000 | Bower et al. | |
| 6,108,838 A | 8/2000 | Connolly et al. | |
| 6,112,349 A | 9/2000 | Connolly | |
| 6,135,105 A | 10/2000 | Lampotang et al. | 128/204.21 |
| 6,158,432 A | 12/2000 | Biondi et al. | 128/204.21 |
| 6,163,908 A | 12/2000 | Vrzalik | |
| 6,253,766 B1 | 7/2001 | Niles et al. | 128/204.24 |
| 6,282,736 B1 | 9/2001 | Hand et al. | |
| 6,282,737 B1 | 9/2001 | Vrzalik | |
| 6,463,930 B2 | 10/2002 | Biondi et al. | 128/204.21 |
| 6,499,160 B2 | 12/2002 | Hand et al. | |
| 6,526,610 B1 | 3/2003 | Hand et al. | |
| 6,566,833 B2 | 5/2003 | Bartlett | |
| 6,584,973 B1 | 7/2003 | Biondi et al. | 128/204.21 |
| 6,609,260 B2 | 8/2003 | Hand et al. | |
| 6,612,995 B2 * | 9/2003 | Leonhardt et al. | 600/532 |
| 6,671,905 B2 | 1/2004 | Bartlett et al. | |
| 6,691,347 B2 | 2/2004 | Hand et al. | |
| 6,701,553 B1 | 3/2004 | Hand et al. | |
| 6,709,405 B2 | 3/2004 | Johnson | 600/538 |
| 6,715,169 B2 | 4/2004 | Niederkrom | |
| 6,728,983 B2 | 5/2004 | Bartlett et al. | |
| 6,732,390 B2 | 5/2004 | Krywiczanin | |
| 6,862,759 B2 | 3/2005 | Hand et al. | |
| 6,862,761 B2 | 3/2005 | Hand et al. | |
| 6,874,181 B1 | 4/2005 | Connolly et al. | |
| 6,934,986 B2 | 8/2005 | Krywiczanin et al. | |
| 7,017,211 B2 | 3/2006 | Krywiczanin et al. | |
| 7,017,574 B2 | 3/2006 | Biondi et al. | 128/204.21 |
| 2006/0037141 A1 | 2/2006 | Krywiczanin et al. | |
| 2006/0162076 A1 | 7/2006 | Bartlett et al. | |
| 2007/0163584 A1 | 7/2007 | Bohm et al. | |

FOREIGN PATENT DOCUMENTS

| | | |
|---|---|---|
| WO | WO 00/33733 | 6/2000 |
| WO | WO 00/44427 | 8/2000 |
| WO | WO 01/93760 A1 | 12/2001 |
| WO | WO 2005/094369 A2 | 10/2005 |

OTHER PUBLICATIONS

Richard et al. Effects of vertical positioning on gas exchange and lung volumes in acute respiratory distress syndrome. Intensive Care Medicine, 2006, vol. 32, pp. 1623-1626.*

Pape HC, et al; Is Early Kinetic Positioning Beneficial for Pulmonary Function in Multiple Trauma Patients?, Injury, Apr. 1998, pp. 219-225, vol. 29, No. 3.

Bein T., et al; Changes in Lung-Chest Wall Compliance in Pressure-Controlled Ventilated Patients During Kinetic Therapy, Clinical Intensive Care, Feb. 1995, pp. 4-8, vol. 6, No. 1.

Bein T., et al; Acute Effects of Continuous Rotational Therapy on Ventilation-Perfusion Inequality in Lung Injury, Intensive Care Medicine, Feb. 1998, pp. 132-137, vol. 24, No. 2.

Bein T., et al; Continuous Axial Rotation and Pulmonary Fluid Balance in Acute Lung Injury, Clinical Intensive Care, Dec. 2000, pp. 307-310, vol. 11, No. 6.

Laubscher, T.P., et al; An Adaptive Lung Ventilation Controller, IEEE Transactions on Biomedical Engineering, Jan. 1994, pp. 51-59, vol. 41, No. 1.

Laubscher, T.P., et al; Automatic Selection of Tidal Volume, Respiratory Frequency and Minute Ventilation in Intubated ICU Patients As Startup Procedure for Closed-Loop Controlled Ventilation, Journal of Clinical Monitoring and Computing, Jan. 1994, pp. 19-30, vol. 11, No. 1.

Leonhardt S.B., et al; Optimal Artificial Ventilation by Identification of Physiological Parameters, Automatisierungstechnik, Jan. 1998, pp. 532-539, vol. 46.

"Over 95% of intubated patients on ASV: Interview with Dr. Jean-Michel Arnal, Regional Hospital, Toulon," User Report, Intelligent Ventilation, *Hamilton Medical AG*, 2006.

"Parameters/Settings; ASV guidelines for adult patients; Adjustments/Weaning," Intelligent Ventilation, *Hamilton Medical AG*, 2006.

Apte et al., "Gastric colonization and pneumonia in intubated critically ill patients receiving stress ulcer prophylaxis: a randomized, controlled trial," *Crit Care Med.*, 20(5):590-593, 1992.

Arnal et al., "ASV in a COPD patient," White Paper, Intelligent Ventilation, *Hamilton Medical AG*, 2005.

Arnal et al., "Utilization of an Automatic Mode of Ventilation (ASV) in a Mixed ICU population: Prospective Observational Study," White Paper, Intelligent Ventilation, *Hamilton Medical AG*, 2005.

Garvey et al., "Effects of gastric alkalization on bacterial colonization in critically ill patients," *Crit Care Med.*, 17(3):211-216, 1989.

International Search Report and Written Opinion issued in International Application No. PCT/US2008/051400, mailed Jun. 24, 2008.

Jackson and Shorr, "Update in ventilator-associated pneumonia," *Curr. Opin. Anaesthesiol.*, 19(2):117-121, 2006.

Kallet and Quinn, "The gastrointestinal tract and ventilator-associated pneumonia," *Respiratory Care*, 50(7):910-923, 2005.

Kollef et al., "A randomized clinical trial of continuous aspiration of subglottic secretions in cardiac surgery patients," *Chest*, 116(5):1339-1346, 1999.

Rello et al., "Reduced burden of bacterial airway colonization with a novel silver-coated endotracheal tube in a randomized multiple-center feasibility study," *Crit Care Med.*, 34(11):2766-2772, 2006.

Safdar et al., "The pathogenesis of ventilator-associated pneumonia: its relevance to developing effective strategies for prevention," *Respiratory Care*, 50(6):725-741, 2005.

* cited by examiner

PROVIDING AUTOMATED OR MANUAL GUIDANCE ON DYNAMIC PATIENT POSITIONING BASED ON MEASURED VARIABLES FOR VENTILATION CONTROL

CROSS-REFERENCE TO RELATED APPLICATIONS

This application claims the priority of U.S. Provisional Patent Application Ser. No. 60/881,907, filed Jan. 23, 2007, the entire disclosure of which is specifically incorporated herein by reference.

FIELD OF THE INVENTION

The present disclosure relates generally to methods and apparatuses for providing therapy to patients with lung conditions. More particularly, the present disclosure relates to methods and apparatuses that incorporate automated control of ventilation and kinetic rotation therapy.

BACKGROUND

The treatment of acute lung failure, acute lung injury (ALI), and acute respiratory distress syndrome (ARDS) is still one of the key problems in the treatment of severely ill patients in the intensive care unit. Despite intensive research over the past two decades, the negative implications of respiratory insufficiency are still affecting both the short and long term outcome of the patient. While different ventilator strategies have been designed to treat the oxygenation disorder and to protect the lungs from ventilator induced lung injury, additional therapeutic options have been evaluated.

Dynamic body positioning (kinetic or axial rotation therapy) was first described by Bryan in 1974. This technique is known to open atelectasis and to improve lung function, particularly arterial oxygenation in patients with ALI and ARDS. Since kinetic rotation therapy is a non-invasive, relatively inexpensive method, and with very limited side effects, it can even be used prophylactically in patients whose overall health condition or severity of injury predispose them to lung injury and ARDS. It could be shown that the rate of pneumonia and pulmonary complications can be reduced while survival increases if kinetic rotation therapy is started early on in the course of a ventilator treatment. This therapeutic approach may reduce the invasiveness of mechanical ventilation (i.e., airway pressures and tidal volumes), the time on mechanical ventilation, and the length of stay on an intensive care unit.

Kinetic rotation therapy in the sense of some exemplary embodiments of the present invention can be applied by use of specialized rotation beds which can be used in a continuous or a discontinuous mode with rests at any desired angle for a predetermined period of time. Examples of such beds are described in whole or in part in the following U.S. patents, all of which are incorporated herein by reference: U.S. Pat. Nos. 4,638,516; 4,763,643; 5,299,334; 4,947,496; 4,730,606; 4,868,937; 6,874,181; 6,112,349; 6,108,838; 6,671,905; 6,566,833; 6,715,169; 7,017,211; 6,934,986; 6,732,390; 6,728,983; 6,701,553; 7,137,160; 6,609,260; 6,862,761; 6,282,736; 6,526,610; 6,499,160; 6,691,347; and 6,862,759. Examples of such beds are also described in whole or in part in the following U.S. patent Publications, all of which are incorporated herein by reference: 20060162076 and 20060037141. A rotation bed that is suitable for adaptation with some exemplary embodiments of the present invention is presently commercialized under the trademark "ROTO-PRONE", commercially available from Kinetics Concepts, Inc., of San Antonio, Tex. ("KCI").

Kinetic rotation therapy in the sense of some exemplary embodiments of the present invention can be applied by use of specialized beds which comprise air cushions provided underneath the patient. Examples of such beds are described in whole or in part in the following U.S. patents, all of which are incorporated herein by reference: U.S. Pat. Nos. 5,142,719; 5,003,654; 5,603,133; 6,282,737; 5,152,021; 5,802,645; and 6,163,908. A rotation bed that is suitable for adaptation with some exemplary embodiments of the present invention is presently commercialized under the trademark "BIODYNE", commercially available from KCI.

A general effect of axial rotation in respiratory insufficiency is the redistribution and mobilization of both intra-bronchial fluid (mucus) and interstitial fluid from the lower (dependent) to the upper (non-dependent) lung areas, which will finally lead to an improved matching of local ventilation and perfusion, also known as V/Q match. As a consequence, oxygenation increases while intra-pulmonary shunt decreases. Lymph flow from the thorax is enhanced by rotating the patient. In addition, kinetic rotation therapy promotes the recruitment of previously collapsed lung areas, thus reducing the amount of atelectasis, at identical or even lower airway pressures. At the same time, now-opened lung areas are protected from the shear stress typically caused by the repetitive opening and closing of collapse-prone alveoli in the dependent lung zones. From H. C. Pape, et al.: "Is early kinetic positioning beneficial for pulmonary function in multiple trauma patients?", Injury, Vol. 29, No. 3, pp. 219-225, 1998 it is known to use the kinetic rotation therapy which involves a continuous axial rotation of the patient on a rotation bed. See also Bein T, et al. Clinical Intensive Care 1995. Bein T, et al. Intensive Care Med 1998. Bein T, et al. Clinical Intensive Care 2000.

It has been found that the kinetic rotation therapy improves the oxygenation in patients with impaired pulmonary function and with post-traumatic pulmonary insufficiency and ARDS.

However, because the kinetic rotation therapy requires a specially designed rotation bed, it has not been found yet that kinetic rotation therapy justifies a broad employment. Further, kinetic rotation therapy has been utilized with standardized treatment parameters, typically equal rotation from greater than 45 degrees to one side to greater than 45 degrees to the other side, and 15 minute cycle times. These rotation parameters are rarely altered in practice due to a lack of conjoint ventilation effectiveness and rotation activity information. Similarly, the lack of conjoint information hampers practitioners from taking advantage of the beneficial effects of kinetic rotation therapy by reducing the aggressiveness of mechanical ventilation parameters employed to treat a rotated patient.

Since positioning therapies such as kinetic rotation therapy and proning are lung-protective and improve oxygenation, ventilation drive parameters need to be adjusted downward in order take full advantage of the benefits of the positioning therapies. The question is how to do so effectively. Prior techniques have viewed ventilation and positioning as separate therapies to be independently titrated to patient needs and responses. For example, a great deal of literature exists on how to optimize PEEP levels based on lung mechanics data, imaging information, patient diagnoses, and other information. None of these methods, though, have recognized the role of positioning therapies in influencing the same measures used to tune ventilation. Similarly, positioning therapies have typically been prescribed upon patient diagnoses without regard to specific information about effectiveness of ventilation.

U.S. application Ser. No. 10/594,400, filed Sep. 26, 2006, and PCT Application No. PCT/US2005/010741, filed Mar. 29, 2005 (published as WO 2005/094369), both of which are incorporated herein by reference, describe methods of combining information from both kinetic and ventilation therapies to allow conjoint analysis of the interaction of each on the other. The references disclose the use of various types of ventilation status information, including respirator measures, hemodynamic measures, and imaging data, in optimizing the two therapies in question.

Instead of using the rotation beds described above for automatically turning and proning a patient to treat ARDS and other lung conditions, some institutions use manual turning of the patient to achieve a similar result. However, there is little guidance to such institutions on when to turn the patient, how long to leave the patient prone, whether leaving the patient at a rotational angle is beneficial, or whether adding a change in pitch is appropriate.

Various methods for the automated control of ventilation are known to those of skill in the art. Examples of such methods which are suitable for use with exemplary embodiments of the present invention are described in Laubscher et al., "An Adaptive Lung Ventilation Controller," IEEE Transactions on Biomedical Engineering, Vol. 41, No. 1, pp. 51-59, 1994 ("Laubscher-1"), and Laubscher et al., "Automatic Selection of Tidal Volume, Respiratory Frequency and Minute Ventilation in Intubated ICU Patients as Startup Procedure for Closed-Loop Controlled Ventilation," Int. J. Clinical Monitoring and Computing, 11:19-30, 1994 ("Laubscher-2"), both of which are incorporated herein by reference. Laubscher-1 describes a closed loop ventilation method called Adaptive Lung Ventilation (ALV), which is based on a pressure controlled ventilation mode suitable for paralyzed, as well as spontaneously breathing, subjects. As explained in Laubscher-1, the clinician enters a desired gross alveolar ventilation ($V'_{gA}$ in 1/min), and the ALV controller tries to achieve this goal by automatic adjustment of mechanical rate and inspiratory pressure level. The adjustments are based on measurements of the patient's lung mechanics and series dead space. Laubscher-2 describes a computerized method for automatically selecting startup settings for closed loop mechanical ventilation. An automated ventilation control algorithm that is suitable for adaptation with some exemplary embodiments of the present invention is presently commercialized under the trademark "Adaptive Support Ventilation" or "ASV", commercially available from Hamilton Medical, Inc., of Reno, Nev.

Other methods of automated ventilation control which are suitable for use with exemplary embodiments of the present invention are described in U.S. Pat. No. 4,986,268 ("Tehrani"), which is incorporated herein by reference. Tehrani describes a method for automatically controlling a ventilator in which the ventilation and breathing frequency requirements of a patient are determined from measurements of several parameters, including the air viscosity factor of the patient's lungs, the barometric pressure, the lung elastance factor of the patient, measured levels of carbon dioxide and oxygen of the patient, and the metabolic rate ratio of the patient.

One problem associated with hospitalized and particularly ventilated patients is pneumonia. The incidence of these pneumonias has been estimated at 9-40% (Safdar et al 2005). One cause of these pneumonias is foreign matter, and particularly infectious matter, entering the lungs. In the case of the ventilated patient this matter enters the lungs around, as well as through, the endotracheal tube used to ventilate the patient. This is generally referred to as ventilator-associated pneumonia.

In addition to ventilator-associated pneumonia, non-ventilated patients are also prone to pneumonia. In these patients aspiration of fluids is often the cause of the pneumonia. This is called aspiration pneumonia. The fluid aspirated can be tracheal, oral, and/or gastric. Small studies by Garvey et al. (1989) and Apte et al. (1992) both show approximately 50% of these pneumonias could be traced to organisms of gastric origin.

Increasingly rigorous and robust studies have shown the enormous cost, morbidity, and mortality of infections acquired in the intensive care unit in general and of ventilator-associated pneumonia in particular (Jackson and Shorr 2006).

Any problems or shortcomings enumerated in the foregoing are not intended to be exhaustive but rather are among many that tend to impair the effectiveness of previously known techniques. Other noteworthy problems may also exist; however, those presented above should be sufficient to demonstrate that apparatuses and methods appearing in the art have not been altogether satisfactory and that a need exists for the techniques disclosed herein.

SUMMARY OF THE INVENTION

In certain exemplary embodiments, the prevent invention comprises a method of controlling the positioning of a patient in or on a patient support surface, comprising: (a) using an artificial ventilator to artificially ventilate one of the patient's lungs, (b) determining the status of the artificially ventilated lung by measuring one or more ventilation status measures, and (c) using one or more of the ventilation status measures to provide feedback for controlling the positioning of the patient. In some exemplary embodiments, the feedback is used for automated control of the positioning of the patient, which in some exemplary embodiments is accomplished using an apparatus comprising a bed that is rotatable about its longitudinal axis, while in other exemplary embodiments the automated control is accomplished using an apparatus comprising a bed that comprises air cushions provided underneath the patient. In still other exemplary embodiments, the feedback is used as guidance for manual control of the positioning of the patient, and in some exemplary embodiments the guidance comprises textual and/or graphical guidance statements.

In certain exemplary embodiments, the ventilation status measures comprise respiratory measures, which in some exemplary embodiments comprise one or more of direct $VO_2$, $paO_2$, and pulmonary mechanics measures. In some exemplary embodiments, the pulmonary mechanics measures comprise one or more of upper and lower inflection points of the expiratory and inspiratory pressure-volume curves and the airway pressure at the point of maximal pressure-volume compliance (Pmax). In other exemplary embodiments, the ventilation status measures comprise hemodynamic measures, which in some exemplary embodiments comprise one or more of $DO_2$, indirect $VO_2$, $SpO_2$, cardiac output, cardiac stroke work, stroke volume, diastolic volumes, pulmonary vascular resistance, pulmonary arterial wedge pressures, pulmonary vascular compliance, $O_2$ extraction ratio, Qs/Qt shunt fraction, and extravascular lung water measures. In still other exemplary embodiments, the ventilation status measures comprise imaging data, which in some exemplary embodiments comprises one or more of electrical impedence tomography (EIT) data and computed tomography (CT) data.

In yet another exemplary embodiment, the method further comprises using one or more of the ventilation status measures as feedback for controlling at least one ventilation parameter of the artificial ventilator. In still another exemplary embodiment, the position of the patient that is controlled is the pitch of the patient's body.

In certain exemplary embodiments, the present invention comprises an apparatus for controlling the positioning of a patient in or on a patient support surface, comprising: (a) an artificial ventilator for artificially ventilating one of the patient's lungs, (b) measuring equipment for determining the status of the artificially ventilated lung by measuring one or more ventilation status measures, (c) one or more information processors that receive the one or more ventilation status measures from the measuring equipment and provide feedback for controlling the positioning of the patient. In some exemplary embodiments, the one or more information processors are computers. In other exemplary embodiments, the feedback is in the form of signals that can be provided to a control unit that controls a bed that is rotatable about its longitudinal axis. In still other exemplary embodiments, the feedback is in the form of signals that can be provided to a control unit that controls a bed that comprises air cushions provided underneath the patient. In yet another exemplary embodiment, the feedback is in the form of textual and/or graphical guidance statements that can be used for manual control of the positioning of the patient. In certain exemplary embodiments, the one or more information processors provide feedback for controlling at least one ventilation parameter of the artificial ventilator.

In certain exemplary embodiments, the artificial ventilator used in the method or apparatus is controlled by the ALV algorithm and the ventilation status measures comprise the information that drives that algorithm, namely the measurements of the patient's lung mechanics and series dead space. In other exemplary embodiments, the artificial ventilator is controlled by an algorithm driven by one or more of the following ventilation status measures: the air viscosity factor of the patient's lungs, the barometric pressure, the lung elastance factor of the patient, measured levels of carbon dioxide and oxygen of the patient, and the metabolic rate ratio of the patient.

Certain exemplary embodiments comprise a method of optimizing ventilation parameters for a patient. In certain exemplary embodiments, the method may comprise: using an artificial ventilator to artificially ventilate a lung of a patient; administering a first ventilation parameter at an initial value; placing the patient in a first position; obtaining a first value of a first physiological parameter when the first ventilation parameters is at the initial value and the patient is in the first position; varying the first ventilation parameter to a subsequent value; and obtaining a second value of the first physiological parameter when the first ventilation parameter is at the subsequent value. Exemplary embodiments may also comprise: placing the patient in a second position; obtaining a third value of the first physiological parameter when the patient is in the second position; defining a cost function based on the initial and subsequent values of the first ventilation parameter, the first and second positions of the patient, and the first, second and third values of the first physiological parameter; and calculating a minimum value of the cost function to determine an optimum value for the first ventilation parameter and for the position of the patient.

Certain exemplary embodiments may also comprise: obtaining a first value of a second physiological parameter when the first ventilation parameter is at the initial value and the patient is in the first position; obtaining a second value of the second physiological parameter when the first ventilation parameter is at the subsequent value; obtaining a third value of the second physiological parameter when the patient is in the second position; and calculating a minimum value of a cost function to determine an optimum value for the first ventilation parameter and for the position of the patient, where the cost function is based on the initial and subsequent values of the first ventilation parameter, the first and second positions of the patient, and the first, second and third values of the first physiological parameter.

In certain exemplary embodiments, the first and second physiological parameters comprise measurements of the patient's lung mechanics and series dead space. In other exemplary embodiments, the first and second physiological parameters are direct measurements that may be combined to yield a more comprehensive quantification of lung performance. In still other exemplary embodiments, the first position may be a different pitch than the second position. In specific exemplary embodiments, placing the patient in a second position comprises raising or lowering the head-end of the patient with respect to the foot-end of the patient. The first position may be a different rotational position than the second position in certain exemplary embodiments, and placing the patient in a second position may comprise rotating a support surface about its longitudinal axis, and/or adjusting an adjustable air cushion supporting the patient.

Certain exemplary embodiments may comprise a control system to automatically adjust the first ventilation parameter and a position of the patient to approximately their optimum values. In certain exemplary embodiments, the first ventilation parameter and a position of the patient are manually adjusted by a caregiver to be administered at approximately the optimum values. Still other exemplary embodiments may comprise an indicator to indicate when the first ventilation parameter and a position of the patient are at approximately the optimum values.

In certain exemplary embodiments, the first physiological parameter may comprise a respiratory parameter, direct $VO_2$, $paO_2$, or pulmonary mechanics measurements. In other exemplary embodiments, the first physiological parameter may comprise one or more of upper and lower inflection points of the expiratory and inspiratory pressure-volume curves and the airway pressure at the point of maximal pressure-volume compliance (Pmax). In still other exemplary embodiments, the first physiological parameter may comprise a hemodynamic parameter.

In still other exemplary embodiments, the first physiological parameter may comprise one or more of $DO_2$, indirect $VO_2$, $SpO_2$, invasive cardiac output, cardiac stroke work, stroke volume, right heart end diastolic volumes, pulmonary vascular resistance, pulmonary capillary pressures, pulmonary vascular compliance, $O_2$ extraction ratio, Qs/Qt shunt fraction, and extravascular lung water measurements. In still other exemplary embodiments, the first physiological parameter may comprise imaging data, and the imaging data may comprise one or more of electrical impedance tomography (EIT) data and computed tomography (CT) data.

In still other exemplary embodiments, the cost function may be defined using one or more of the following measurements: the air viscosity factor of the patient's lungs, the barometric pressure, the lung elastance factor of the patient, the measured levels of carbon dioxide and oxygen of the patient, and the metabolic rate ratio of the patient.

Still other exemplary embodiments may comprise a method of optimizing treatment for a patient. In certain exemplary embodiments, the method may comprise a support surface configured for placement in a first position and a second position; an artificial ventilator configured to artificially ventilate a lung of the patient; measuring equipment configured to obtain values for one or more physiological parameters, ventilation parameters, and position parameters; a feedback system configured to send the values for the one or more physiological parameters, ventilation parameters, and position parameters to an analysis system, wherein the analysis system is configured to calculate a cost function based on the values for the one or more physiological parameters, ventilation parameters, and position parameters; and a control system configured to adjust the one or more ventilation parameters and position parameters to minimize the cost function.

In certain exemplary embodiments, the support surface may be rotatable about its longitudinal axis, and/or the support surface may comprise adjustable air bladders. In still other exemplary embodiments, the control system may automatically adjust the one or more ventilation parameters and the position parameters to minimize the cost function. In specific exemplary embodiments, the control system may comprise manual adjustments by a caregiver and an audible or visible indicator that indicates when the one or more ventilation parameters and position parameters are adjusted so that the cost function is minimized. In certain exemplary embodiments, the support surface may be configured to adjust the pitch of the patient.

Still other exemplary embodiments may comprise: using an artificial ventilator to artificially ventilate a lung of the patient; measuring a physiological parameter; and adjusting the pitch of the patient to optimize the physiological parameter. Certain exemplary embodiments may comprise measuring a ventilation parameter and adjusting the ventilation parameter and the pitch of the patient to optimize the physiological parameter. Still other exemplary embodiments may comprise defining a cost function based on the physiological parameter, the ventilation parameter and the pitch of the patient; determining a minimum value of the cost function; and adjusting the ventilation parameter and the pitch of the patient to minimize the value of the cost function.

BRIEF DESCRIPTION OF THE DRAWINGS

While exemplary embodiments of the present invention have been shown and described in detail below, it will be clear to the person skilled in the art that changes and modifications may be made without departing from the scope of the invention. As such, that which is set forth in the following description and accompanying drawings is offered by way of illustration only and not as a limitation. The actual scope of the invention is intended to be defined by the following claims, along with the full range of equivalents to which such claims are entitled. In addition, one of ordinary skill in the art will appreciate upon reading and understanding this disclosure that other variations for the invention described herein can be included within the scope of the present invention.

In the following Detailed Description of Exemplary Embodiments, various features are grouped together in several exemplary embodiments for the purpose of streamlining the disclosure. This method of disclosure is not to be interpreted as reflecting an intention that exemplary embodiments of the invention require more features than are expressly recited in each claim. Rather, as the following claims reflect, inventive subject matter lies in less than all features of a single disclosed exemplary embodiment. Thus, the following claims are hereby incorporated into the Detailed Description of Exemplary Embodiments, with each claim standing on its own as a separate embodiment.

Figure 1:
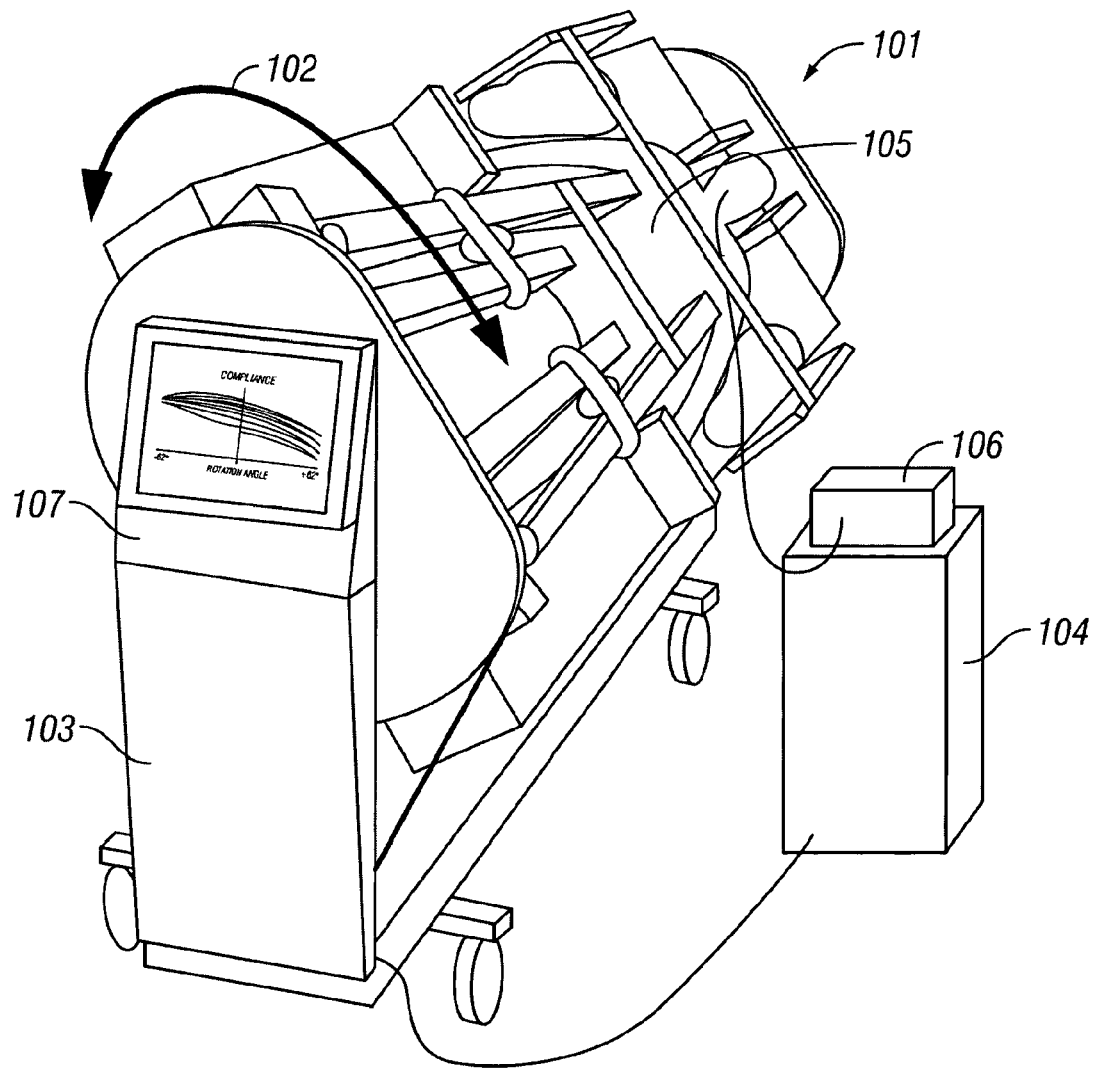

The following drawings illustrate by way of example and not limitation. Identical reference numerals do not necessarily indicate an identical structure. Rather, the same reference numeral may be used to indicate a similar feature or a feature with similar functionality. Not every feature of each exemplary embodiment is labeled in every figure in which that exemplary embodiment appears, in order to keep the figures clear.

FIG. 1 shows an example of an apparatus according to some exemplary embodiments of the present invention.

Figure 2:
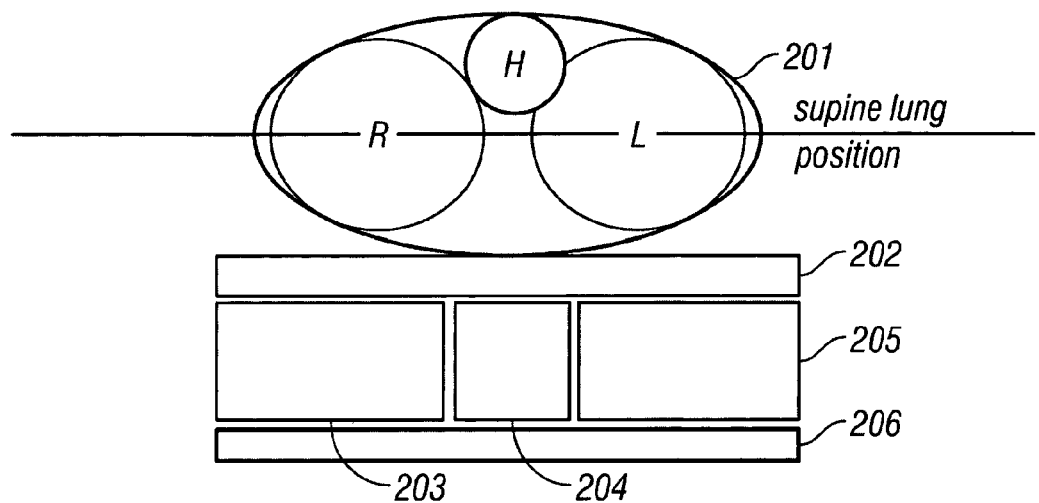

FIG. 2 shows a first example of a position actuator in a horizontal position.

Figure 3:
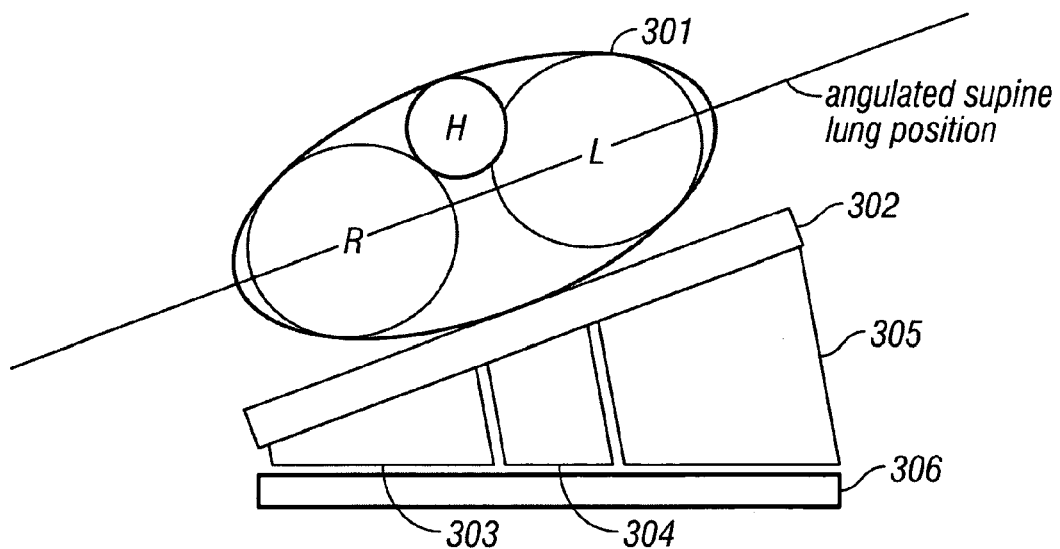

FIG. 3 shows the first example of a position actuator in an angulated position.

Figure 4:
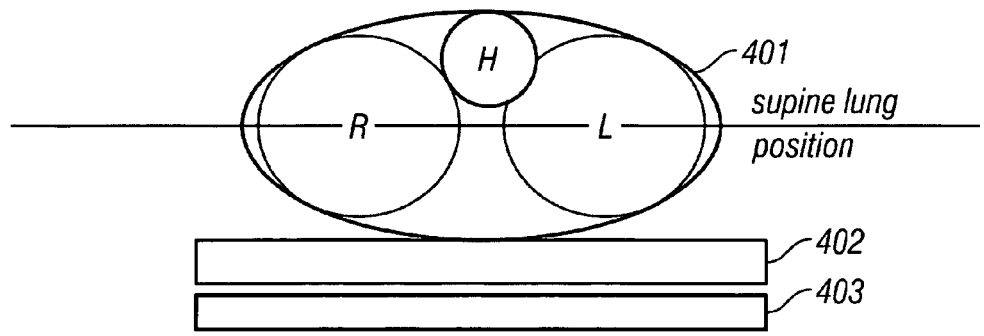

FIG. 4 shows a second example of a position actuator in a horizontal position.

Figure 5:
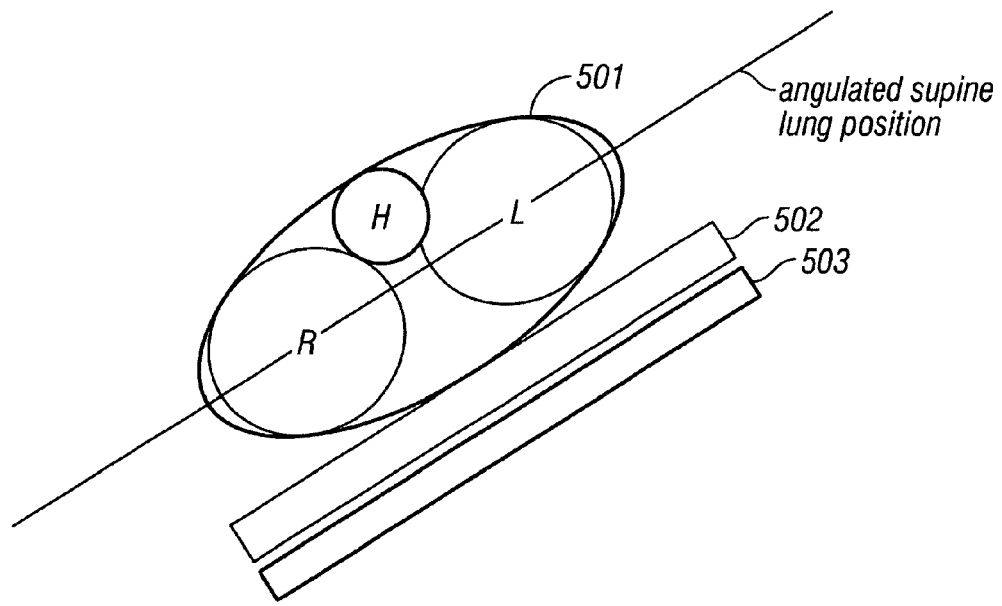

FIG. 5 shows the second example of a position actuator in an angulated position.

Figure 6:
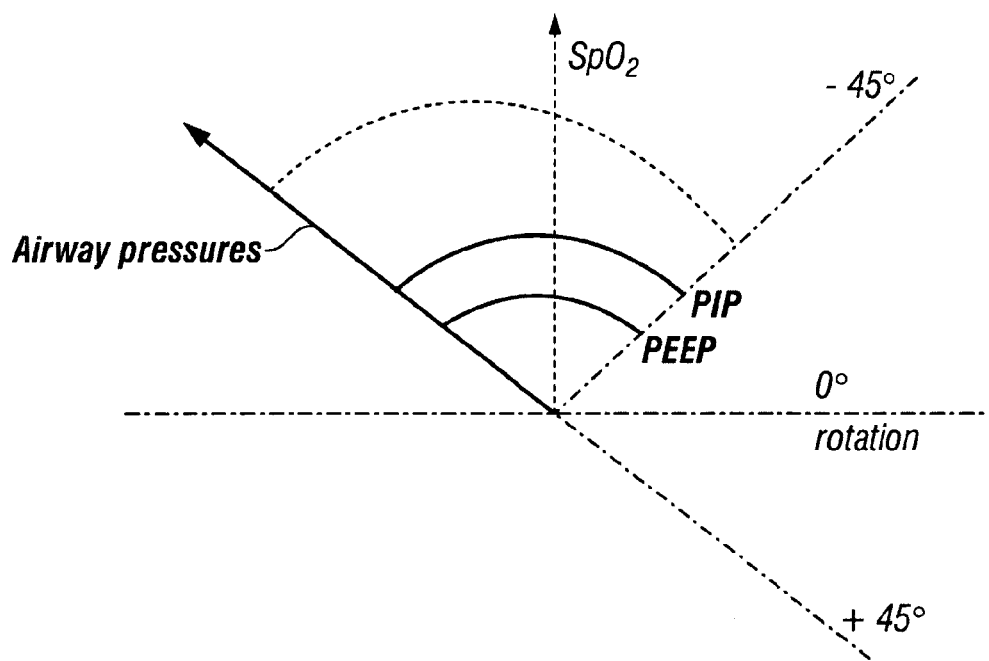

FIG. 6 shows a schematic monitoring screen for the method for controlling at least one ventilation pressure.

Figure 7:
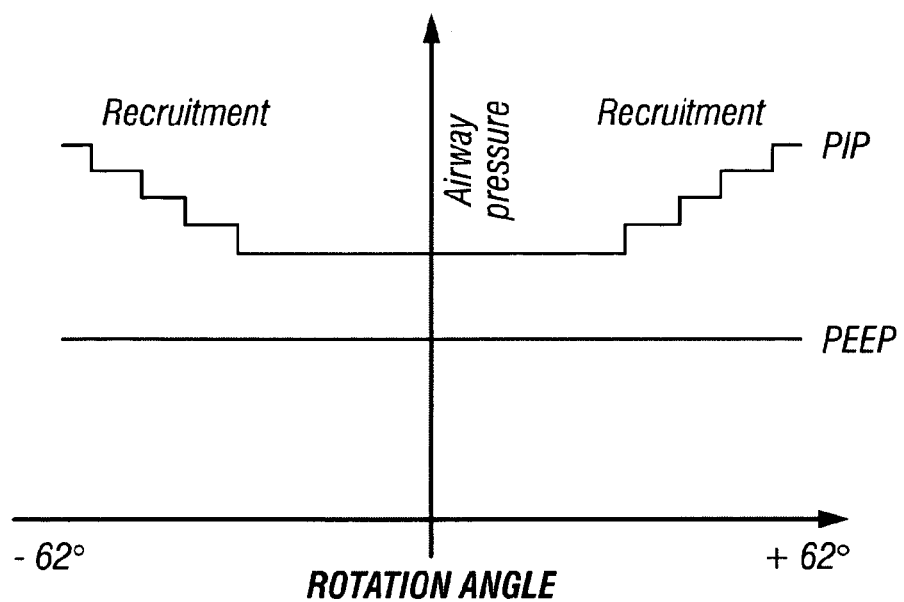

FIG. 7 shows an alveolar recruitment maneuver during kinetic rotation therapy.

FIGS. 8A-8D show the titration process after a successful lung recruitment maneuver has been performed during kinetic rotation therapy.

Figure 9:
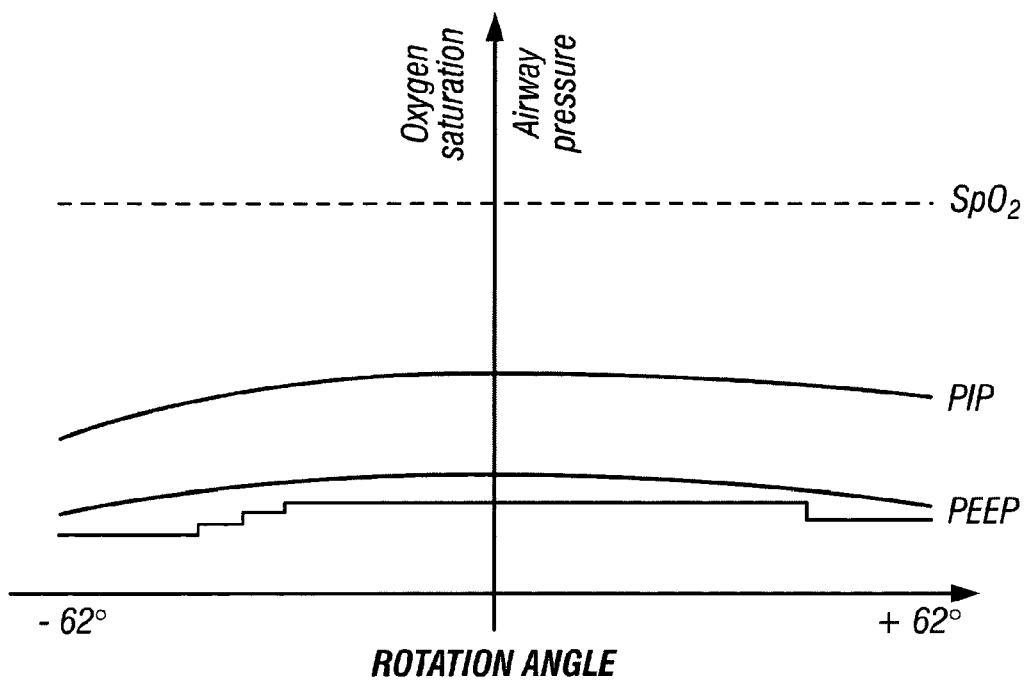

FIG. 9 shows an artificial ventilation of a lung by controlling the PIP and the PEEP in accordance with the rotation angle.

Figure 10:
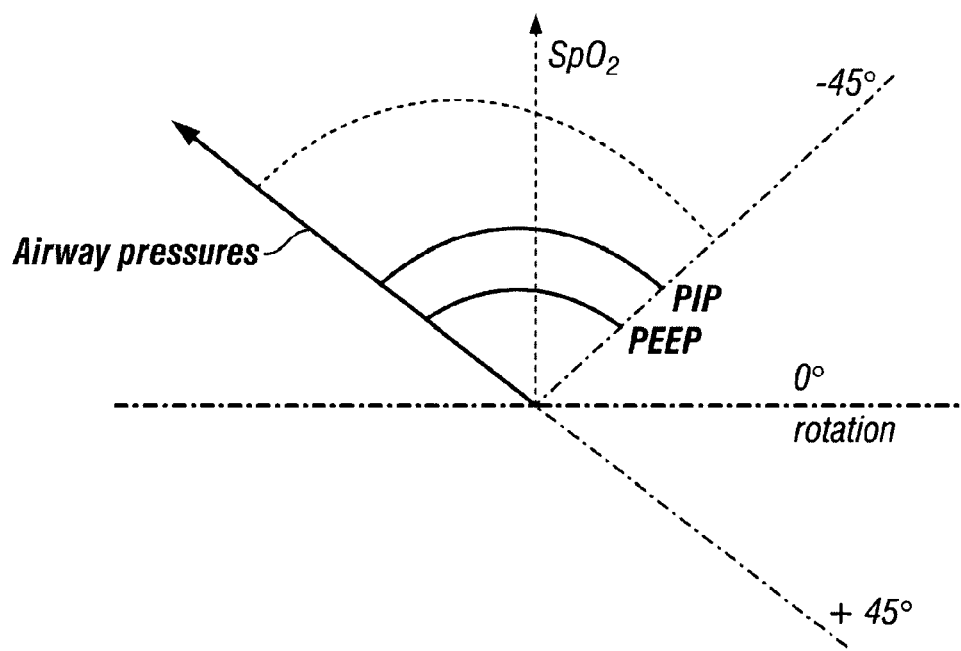

FIG. 10 shows a schematic monitoring screen when controlling the PIP and PEEP during the rotation cycle according to FIG. 9.

Figure 11:
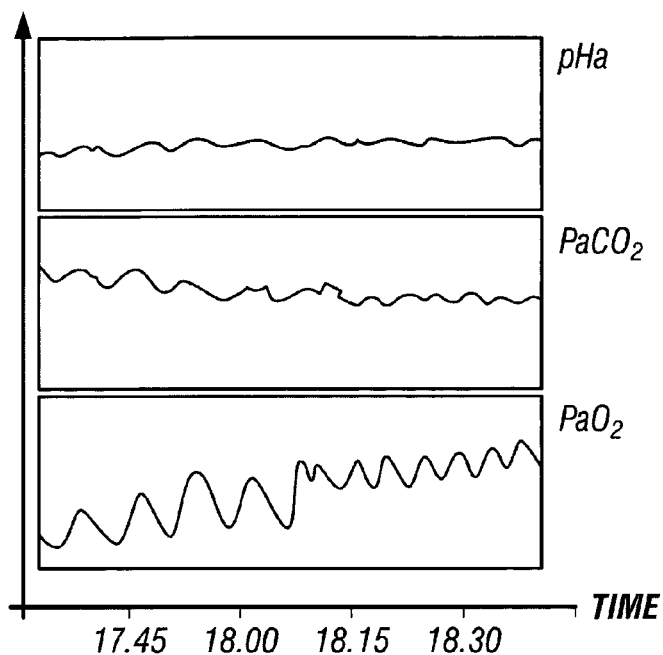

FIG. 11 shows the measurements of $paO_2$, $paCO_2$, and pHa during the kinetic rotation therapy.

Figure 12:
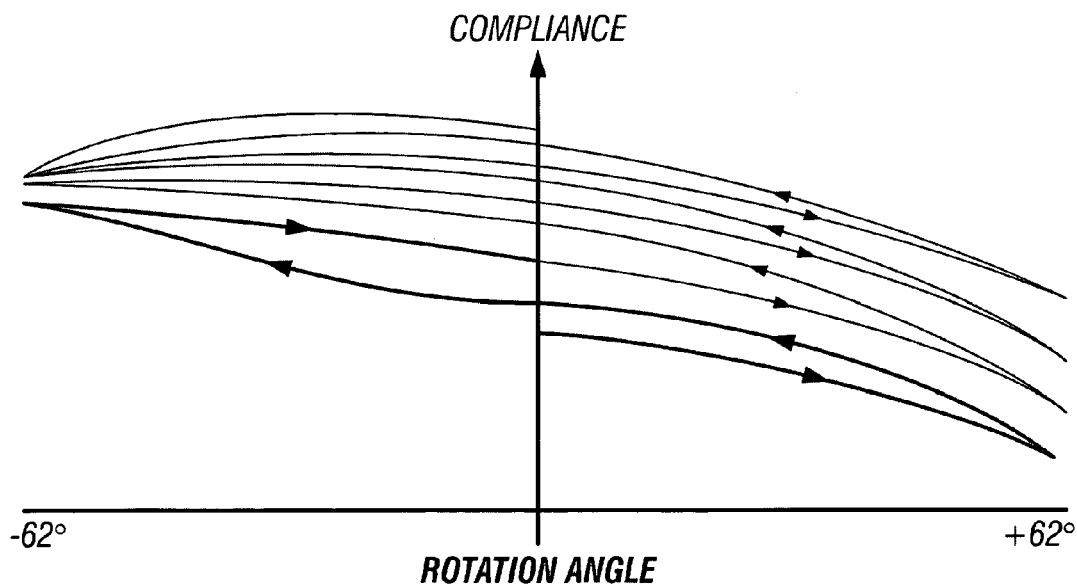

FIG. 12 shows the measurement of compliance during kinetic rotation therapy.

Figure 13:
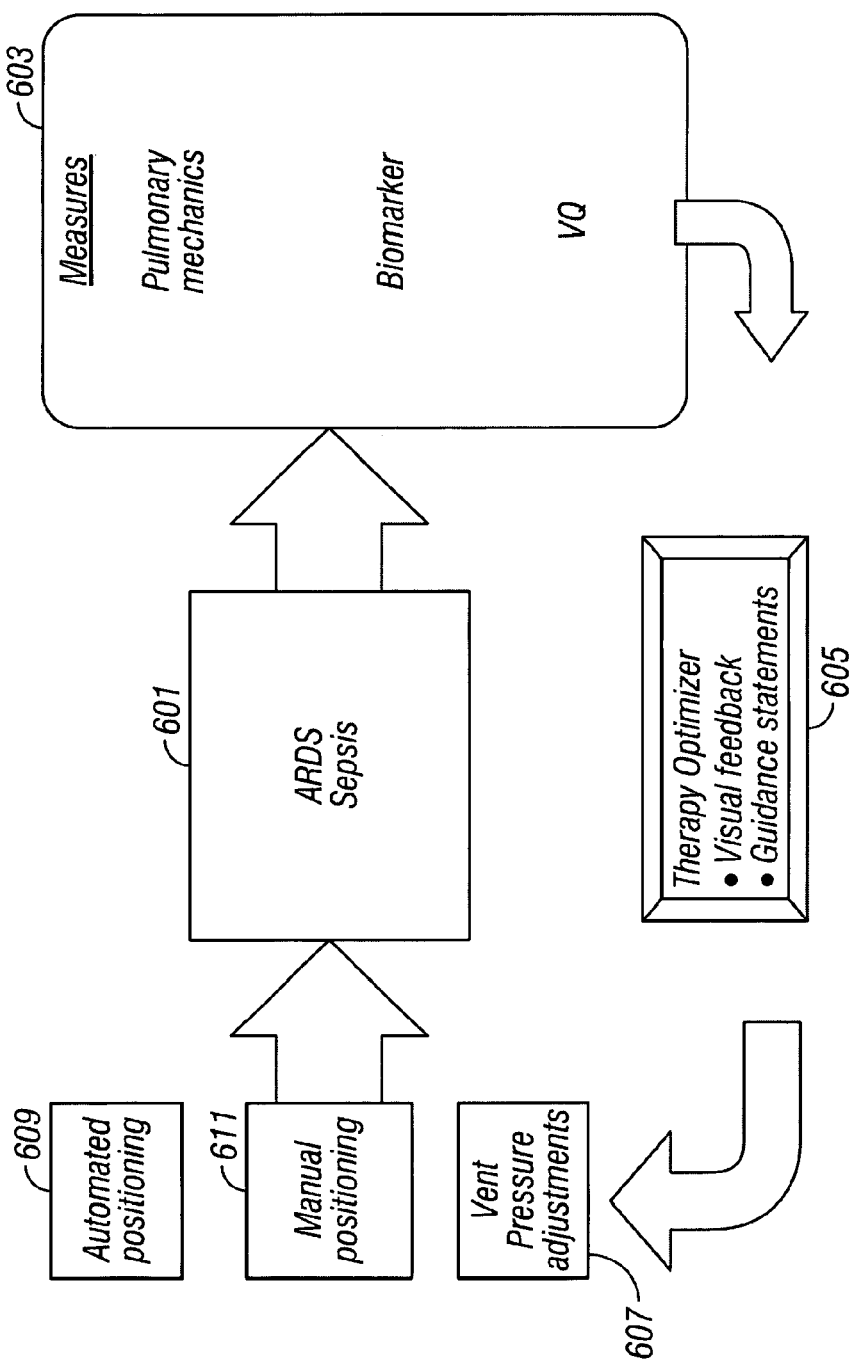

FIG. 13 shows a schematic diagram of one exemplary embodiment of a method for controlling the positioning of a patient in or on a patient support surface.

DETAILED DESCRIPTION OF EXEMPLARY EMBODIMENTS

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, an apparatus or method that "comprises," "has," "contains," or "includes" one or more elements possesses those one or more elements, but is not limited to possessing only those one or more elements or steps. Likewise, an element of an apparatus or method that "comprises," "has," "contains," or "includes" one or more features possesses those one or more features, but is not limited to possessing only those one or more features. Furthermore, a structure that is configured in a certain way must be configured in at least that way, but also may be configured in a way or ways that are not specified.

The terms "a" and "an" are defined as one or more than one unless this disclosure explicitly requires otherwise. The terms "substantially" and "about" are defined as at least close to (and includes) a given value or state (preferably within 10% of, more preferably within 1% of, and most preferably within 0.1% of). Metric units may be derived from the English units provided by applying a conversion and rounding to the nearest millimeter.

The methods and apparatuses of the present invention provide for the use of physiological or physical parameters employed for use in the automated control of ventilation as feedback for either the automated control or the guidance for manual control of the positioning of a patient in or on a patient support surface. Methods and apparatuses may control the roll of the patient (i.e. the rotation of the patient along the patient's longitudinal axis) as well as the pitch of the patient (i.e. the elevation of the patient's head in relation to the patient's feet).

FIG. 1 shows an example of a apparatus according to some exemplary embodiments of the invention. The bed 101 is mounted such that it can be rotated around its longitudinal axis, as indicated by the arrow 102. The rotation angle is changeable by a position actuator 103, which is controlled by a control unit 104.

The patient 105 is fixed on the bed 101 and is artificially ventilated by the ventilator 106. The position actuator 103 can be controlled by the control unit 104 such that the patient is turned resulting in a defined lung position of the artificially ventilated lung. The lung position refers to the rotation angle of the lung being 0° if the patient is lying horizontally on the bed, which itself is positioned horizontally. Measurements of the lung position can be performed by employing a portable position sensor attached to the patient's thorax and connected to the control unit 104. The bed 101 shown in FIG. 1 also allows one to determine the rotation angle of the patient's lung through a measurement of the rotation angle of the bed 101.

The status of the artificially ventilated lung can be determined by a variety of methods using a suitable measurement device 107. The measurement device 107 can for example use data such as airway pressures, constitution of the expired gas, and the volume of the inspired and expired gas obtained from the artificial ventilator to determine the status of the lung. The measurements to determine the status of the lung can either be performed continuously or sporadically at defined lung positions. Examples of methods to determine the status of the lung are given below:

The status of the lung is determined on the basis of the $CO_2$ concentration of the expired gas over a single breath. Such a method and apparatus are known from the European patent application EP04007580.6, filed on 26 Mar. 2004, which is incorporated herein by reference.

The status of the lung is determined on the basis of the hemoglobin oxygen saturation ($SO_2$). This can be carried out by means of a saturation sensor. Advantageously, a feedback control loop controls the inspiratory oxygen fraction ($FiO_2$) at the artificial ventilator such that the hemoglobin oxygen saturation ($SO_2$) is kept constant and a data processor determines during a change of the airway pressure from the course of the controlled inspiratory oxygen fraction ($FiO_2$) an airway pressure level which corresponds to alveolar opening or alveolar closing of the lung. Such a method and apparatus are known from WO 00/44427 A1, which is incorporated herein by reference.

The status of the lung is determined on the basis of the $CO_2$ volume exhaled per unit time. Such a method and apparatus are known from WO 00/44427 A1, which is incorporated herein by reference.

The status of the lung is determined on the basis of the endtidal $CO_2$ concentration. Such a method and apparatus are known from WO 00/44427 A1, which is incorporated herein by reference.

The status of the lung is determined on the basis of the arterial partial pressures of oxygen $paO_2$. Such a method and apparatus are known from S. Leonhardt et al., "Optimierung der Beatmung beim akuten Lungenversagen durch Identifikation physiologischer Kenngrößen", at 11/98, pp. 532-539, 1998, which is incorporated herein by reference.

The status of the lung is determined on the basis of the compliance of the lung, wherein the compliance can be defined by the tidal volume divided by the pressure difference between peak inspiratory pressure and positive end-expiratory pressure (PIP-PEEP). Definitions of the compliance are known, e.g., from WO 00/44427 A1, which is incorporated herein by reference.

The status of the lung is determined on the basis of the inspiratory and/or expiratory dynamic airway resistance, wherein these resistances can be defined as the driving pressure difference divided by the flow of breathing gases ($cmH_2O/l/s$). Definitions of the resistance are known, e.g., from WO 00/44427 A1, which is incorporated herein by reference.

The status of the lung is determined on the basis of electrical impedance tomography data. Such a method and apparatus are known from WO 00/33733 A1 and WO 01/93760 A1, which are incorporated herein by reference.

In the following discussion, one exemplary embodiment an apparatus and method of treatment of the patient will be described which will be explained thereafter in more detail by means of the FIGS. 2-12.

Recruitment Maneuver

In this exemplary embodiment, at 0° rotation angle PEEP is adjusted above the expected alveolar closing pressure (depending on the lung disease, between 15 and 25 $cmH_2O$). PIP is set sufficiently high above PEEP to ensure adequate ventilation.

Rotation is then started and each lung is opened separately while it is moved into the upward position.

With increasing rotation angle, a stepwise increase of the PIP starts 5-20 breaths prior to reaching the maximum rotation angle. PIP reaches its maximum value (depending on the lung disease, between 45 and 65 $cmH_2O$) at the maximum rotation angle.

Having crossed the maximum rotation angle, PIP is decreased within 5-20 breaths.

After each lung has been recruited separately (by rotating the patient to both sides) in the above manner, PIP is adjusted for each lung separately to maintain adequate ventilation.

PEEP Titration for Finding the Closing PEEP

In this exemplary embodiment, after a recruitment maneuver, PEEP is decreased continuously with increasing rotation angles. The status of the artificially ventilated lung is recorded continuously. Starting at a given PEEP at a rotation angle of 0°, PEEP will be lowered such that at maximum rotation angle PEEP will be reduced by 1-2 $cmH_2O$ (procedure 1). If no signs for alveolar collapse occur in any of the above signals, the level of PEEP is recorded and will be increased continuously to the previous setting when at 0°. While turning the patient to the other side PEEP is reduced in the same way (procedure 2). If no signs for alveolar collapse occur in any of the above signals, the level of PEEP is then kept at this value and the patient is turned back to 0°.

If no collapse is present at a rotation angle of 0°, the procedures 1 and 2 are carried out at reduced PEEP levels until signs of alveolar collapse occur. The level of PEEP at which this collapse occurs is then recorded for the respective side. The PEEP will be increased continuously to the previous setting when at 0° while turning the patient back to 0°. If signs of a lung collapse are still present due to a hysteresis behavior of the lung, a recruitment maneuver will be performed at this stage to re-open the lung as described above.

Continuing with an open lung condition, the PEEP is set 2 cmH$_2$O above the known closing pressure for the side for which the lung collapse occurred.

Thereafter, PEEP is reduced in the way described above while turning the patient to the opposite side for which the closing pressure is not yet known. Once collapse occurs also for this side, PEEP is recorded and the lung is reopened again.

Controlling the Ventilation Parameters During Rotation

In this exemplary embodiment, after having determined the PEEP collapse pressure of each side, PEEP will be adjusted continuously with the ongoing rotation while making sure that PEEP never falls below the levels needed for each one of the sides.

Since PEEP and compliance may vary with the rotation angle, adjustments are needed. Therefore, during rotation therapy PIP levels are adjusted continuously from breath to breath in accordance with the difference between a first status and a second status of the artificially ventilated lung in order to ventilate the patient sufficiently while keeping tidal volumes within a desired range of 6-10 ml/kg body weight.

Furthermore, if PIP pressures are at very low values already, it might be advisable to leave PIP constant but adjust for changes in compliance by adjusting the respiratory rate (RR). Then, RR is adjusted continuously from breath to breath in order to ventilate the patient sufficiently while keeping PIP constant.

It has been shown that the variation of the rotation period improves the effect of the kinetic rotation therapy even further. For example, the following modes of variation can be applied:

Sinusoidal variation with wave length between several minutes to several hours with set minimum and maximum values for ration angles, speeds, and resting periods.

Ramp like variation within certain boundaries with ramp periods between several minutes to several hours and set minimum and maximum values for rotation angles, speeds, and resting periods. Random variation about a given mean value at a single level of variability (i.e., biologic variability) with amplitudes between 50% to 200% of mean sequence of magnitude of this parameter from a uniform probability distribution between, e.g., 0% to 100% of its chosen mean value.

Variability can be determined according to technical approaches covering the whole range from allowed minimum to maximum.

Distribution of rotation parameters can be Gaussian or biological.

In addition to the rotation period, the rotation angle, the rotation speed, and the resting periods can be varied. In order to adjust for variable rotation angles, speed and resting times, a mean product of angle and resting period, etc. can be defined, which needs to be kept constant. For example:

While rotation angle randomly varies about a given rotation angle, resting periods are adjusted to keep the product of angle and time approximately constant at a given rotation speed.

While rotation angle randomly varies about a given rotation angle, rotation speed is adjusted to keep the product of angle and speed approximately constant while no resting period is applied.

FIG. 2 shows a first example of a position actuator in a horizontal position representing the initial position. The schematic drawing depicts the patient 201 lying in the supine position. As defined in medical imaging, the patient is looked at from the feet, thus the right lung (R) is on the left hand side of FIG. 2, and the left lung (L) is on the right hand side of FIG. 2, while the heart (H) is located centrally and towards the front.

It should be noted in this connection that the methods according to the invention can be equally well applied to patients lying in the prone position.

The patient 201 is lying on a supporting surface 202, which covers three air-cushions 203, 204, and 205. These air-cushions, being mounted to the fixed frame 206 of the bed, are inflated in this horizontal position of the bed with a medium air pressure. The air pressure of the air-cushions 203, 204, and 205 can be adjusted by a control unit either by pumping air into an air-cushion or by deflating an air-cushion. Those of ordinary skill in the art would understand that other fluids than air could be used, as well.

Changing the air pressure in the air-cushions 203, 204, and 205 in a particular fashion leads to a rotation of the supporting surface 202 and hence, to a rotation of the artificially ventilated lung. By simultaneous measurements of the rotation angle of the artificially ventilated lung, i.e., through an attached position sensor at the patient's thorax, the rotation angle of the artificially ventilated lung can be adjusted to defined positions. Alternatively, a defined lung position can be reached by a predetermined step size of the position actuator, i.e., a predetermined air pressure within each air-cushion.

FIG. 3 shows the first example of the position actuator in an angulated position resulting from a specific setting of the air pressures in the air-cushions. Compared to FIG. 2, in this particular example the air pressure of the air-cushion 303 has been lowered, the air pressure of the air-cushion 304 has not been changed, and the air pressure of the air-cushion 305 has been raised.

This results in a rotation of the supporting surface 302 and patient 301 thus in a rotation of the artificially ventilated lung. Noticeably, the frame 306 of the bed remains in its horizontal position.

FIG. 4 shows a second example of a position actuator in a horizontal position representing the initial position. The schematic drawing depicts the patient 401 lying in the supine position as defined in the description of FIG. 2.

The patient is lying on a supporting surface 402, which is attached to the frame 403 of the bed. The frame 403 can be rotated by a motor which represents the position actuator according to signals received from a control unit. A rotation of the frame 403 results directly in a rotation of patient 401 and hence the artificially ventilated lung. By simultaneous measurements of the rotation angle of the artificially ventilated lung, i.e., through measurements of the rotation angle of the frame 403, the rotation angle of the artificially ventilated lung can be adjusted to defined positions. Alternatively, a defined lung position can be reached by a predetermined step size of the position actuator, i.e., performing a predetermined number of steps using a step motor.

FIG. 5 shows the second example of a position actuator in an angulated position, resulting from a specific setting of the position actuator. In this particular setting of the position actuator the left lung of the patient 501 is elevated. The supporting surface 502 and the frame 503 of the bed are both rotated.

FIG. 6 shows a schematic monitoring screen for the method for controlling at least one ventilation pressure. Displayed are both the input of the artificial ventilation system in form of the PIP and the PEEP as well as an example of a physiological output information of the patient in form of the on-line SpO$_2$ signal. The SpO$_2$ signal represents the oxygen saturation level. The values of the PIP, the PEEP, and SpO$_2$ are plotted in a circular coordinate system over the rotation angle of the artificially ventilated lung. The rotation angle is depicted in FIG. 6 through the dashed lines for values of −45°, 0°, and 45°. The values for the PIP, the PEEP, and $SpO_2$ can be obtained from the graph using an axis perpendicular to the axis of the particular rotation angle.

As can be seen from FIG. 6, when the bed turns the patient towards a negative rotation angle, the value of the $SpO_2$ signal increases substantially, whereas the value of the $SpO_2$ signal decreases when the patient is turned towards a positive rotation angle.

This variation of the $SpO_2$ signal relates to constant values of the PIP and the PEEP. Without changing at least one of the airway pressures, the evaluation of the $SpO_2$ signal of the patient during a rotation would only represent a diagnostic goal. Therefore, FIGS. 7-10 represent the effects of controlling at least one ventilation pressure on a physiological output information.

FIG. 7 shows an alveolar recruitment maneuver during kinetic rotation therapy. Before the recruitment maneuver starts at 0° rotation angle, the PEEP is adjusted above the expected alveolar closing pressure (depending on the lung disease, between 15 and 25 $cmH_2O$). The PIP is set sufficiently high above the PEEP to ensure adequate ventilation.

During the recruitment maneuver the PIP is stepwise increased such that as many lung units as possible are re-opened, while at the same time the PEEP is maintained at a level to keep the newly recruited lung units open. The recruitment is applied towards the maxima of the positive and the negative rotation amplitudes where the respective upper lung is relieved from almost all superimposed pressures. Therefore, each lung is opened separately while it is moved into the upward position.

For example, the stepwise increase of the PIP can start 5-20 breaths prior to reaching the maximum rotation angle and the PIP reaches its maximum value (depending on the lung disease, between 45 and 65 $cmH_2O$) at the maximum rotation angle. Having crossed the maximum rotation angle the PIP is decreased within 5-20 breaths to its initial value.

After each lung has been recruited separately (by rotating the patient to both sides) in the above manner, PIP can be adjusted for each lung separately to maintain adequate ventilation.

FIG. 8 shows a titration process after a successful alveolar recruitment maneuver has been performed during kinetic rotation therapy.

Due to the hysteresis behavior of the lung, the values obtained for the PIP and for the PEEP during the alveolar recruitment maneuver are too high to further ventilate the lung with these airway pressures once the lung units have been recruited. Thus they need to be reduced systematically during the titration process. The goal is to obtain the minimum values for the PEEP for specific rotation angles that would just keep all lung alveoli open. For further ventilation the PEEP can be set slightly above these values and the PIP can be adjusted according to the desired tidal volume.

Figure 8A:
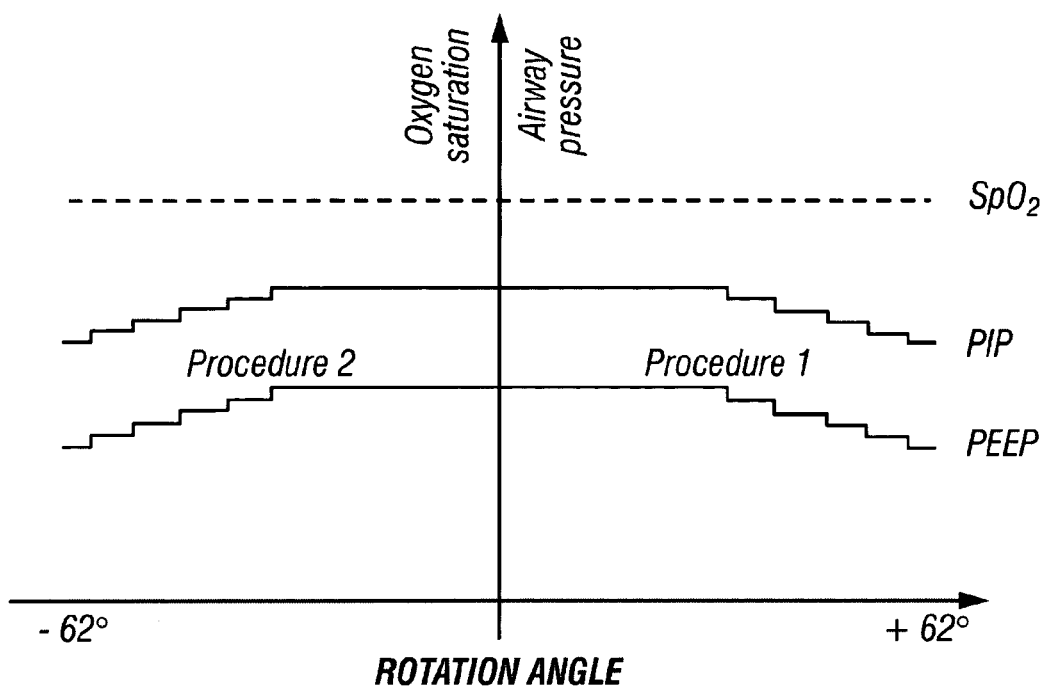

As shown in FIG. 8A, the PIP and the PEEP are reduced, typically in periods of one step-wise reduction per minute, towards both maxima of the rotation amplitude. The titration process begins with decreasing the PIP and/or the PEEP when rotating the artificially ventilated lung towards positive rotation angles (procedure 1). When the artificially ventilated lung is returned to the initial position, i.e., 0° rotation angle, the PIP and the PEEP are set to their initial values. The PIP and/or the PEEP are reduced again once the artificially ventilated lung is rotated towards negative rotation angles (procedure 2). As an example of a physiological feedback parameter the oxygen saturation signal $SpO_2$ is shown in FIG. 8A as a dashed line. The oxygen saturation remains constant during the entire rotation cycle (procedure 1+procedure 2), indicating that no significant collapse occurred. Thus the titration process should continue.

Figure 8B:
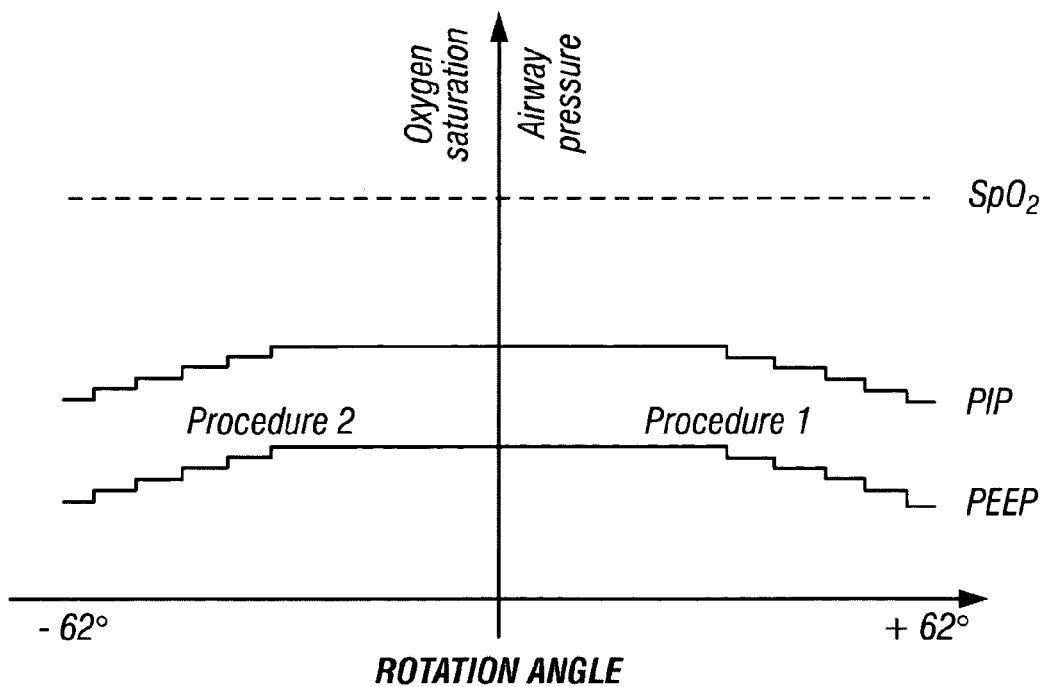

In order to increase the likelihood of a collapse of lung units, each subsequent rotation cycle starts with lower values for the PIP and for the PEEP. FIG. 8B represents a further rotation cycle of the titration process. The oxygen saturation signal $SpO_2$ remains again constant during the rotation cycle shown in FIG. 8B, indicating that the lowest values of the PEEP reached at the maximum rotation angles are still too high to result in a significant collapse of lung units.

Figure 8C:
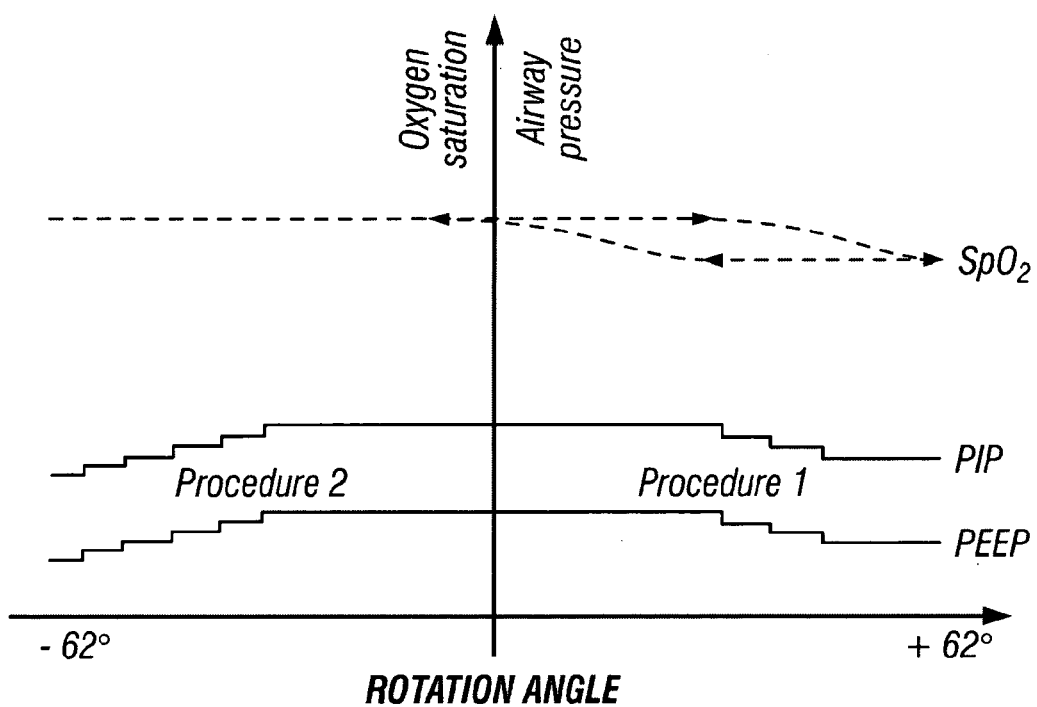

A further reduction of the PIP and the PEEP has been performed before commencing the next rotation cycle as shown in FIG. 8C. When turning the patient to positive rotation angles and reducing the PEEP (procedure 1), the oxygen saturation signal $SpO_2$ shows a variation in form of a reduction. Once this variation has been identified, no further reductions of the airway pressures are performed. The PEEP corresponding to the point when the variation of the oxygen saturation signal $SpO_2$ has been identified represents the collapse pressure for the particular rotation angle. The titration process for positive rotation angles is finished.

When turning the patient back towards the initial position, i.e., 0° rotation angle, the PIP and the PEEP are set to their original values. The oxygen saturation signal $SpO_2$ recovers to its initial value. As indicated in FIG. 8C, a hysteresis effect is usually present.

When turning the patient to negative rotation angles the PIP and/or the PEEP are reduced in order to identify the collapse pressure for negative rotation angles (procedure 2). The oxygen saturation signal $SpO_2$ remains constant, indicating that the value of the PEEP reached at the maximum negative rotation angle is still too high to result in a significant collapse of lung units. Consequently, the titration process at negative rotation angles has to continue.

Figure 8D:
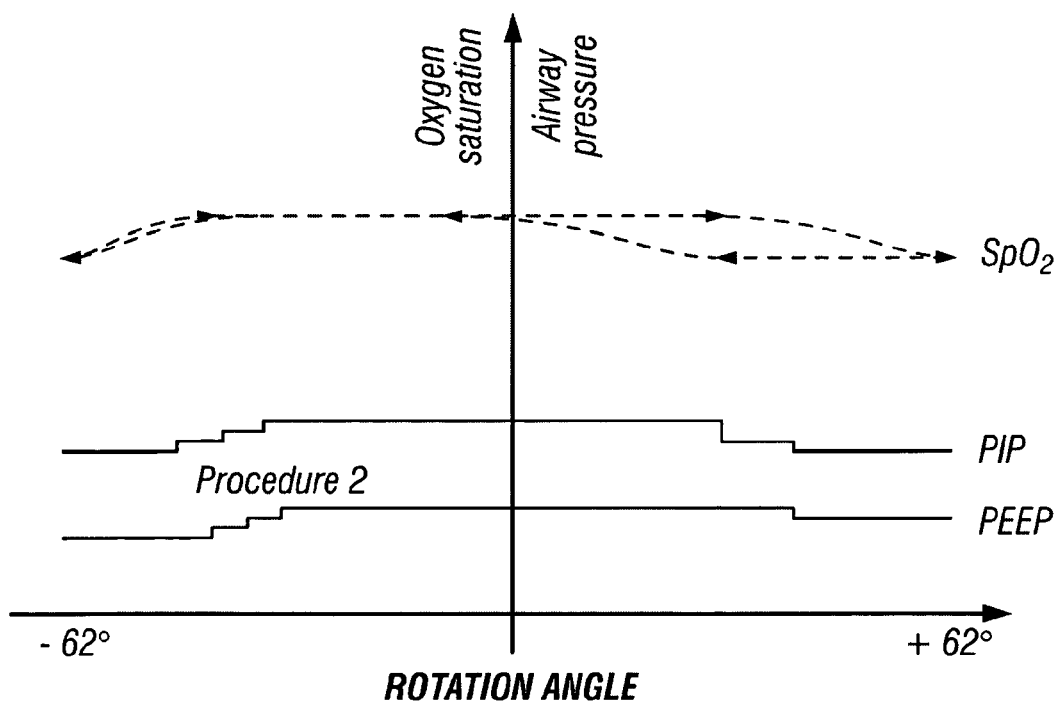

A further rotation cycle starting once more with lower values for the PIP and for the PEEP is shown in FIG. 8D. As indicated, collapse pressures for positive and for negative rotation angles can be identified according to the procedure of FIG. 8C. The collapse pressure for the positive rotation angle, corresponding to the value already obtained in FIG. 8C, is lower than the collapse pressure for the negative rotation angle.

After having identified the collapse pressures for positive and negative rotation angles, a recruitment maneuver according to FIG. 7 needs to be carried out in order to re-open lung units which collapsed during the titration process. As mentioned before, such a re-opening procedure can become necessary already during the titration process once the collapse pressure for one side has been identified. This is the case, if, due to a hysteresis behavior of the lung, signs of lung collapse continue to be present when the patient is turned back to 0° and the PEEP is raised to its previous setting when at 0°.

Once the lung is fully recruited again, the PEEP levels are set for the positive and negative rotation angles separately according to the collapse pressures as identified before. A safety margin of, e.g., 2 $cmH_2O$ is added to each collapse pressure. Eventually, the PIP can be adjusted according to the desired tidal volume.

FIG. 9 shows an artificial ventilation of a lung by controlling the PIP and the PEEP in accordance with the rotation angle. Based on the collapse pressures for positive and for negative rotation angles, as identified according to FIG. 8, a curve for the PEEP as a function of the rotation angle can be established. The shape of the curve, having in this particular example a smooth curvature, can be chosen freely, provided a safety margin is realized in order to keep the PEEP above the corresponding collapse pressure. The curve of the PIP as a function of the rotation angle follows directly from the corresponding PEEP value and the desired tidal volume. Controlling the PIP and the PEEP as a function of the rotation angle in this way leads to an optimal ventilation of the lung. The oxygen saturation signal $SpO_2$ remains constant during the rotation cycle while at the same time, due to the lowest possible values for the PIP and the PEEP, no lung overdistension is present and the desired tidal volume is achieved.

FIG. 10 shows a schematic monitoring screen when controlling the PIP and the PEEP during the rotation cycle according to FIG. 9. The presentation of the PIP, the PEEP, and the $SpO_2$ with respect to the rotation angle is identical to that of FIG. 6.

By controlling the PIP and the PEEP according to the rotation angle it is possible to keep the oxygen saturation signal $SpO_2$ constant during a rotation cycle. This is in contrast to FIG. 6 where the oxygen saturation signal $SpO_2$ decreased with increasing rotation angles, i.e. due to the collapse of lung units. This collapse is prevented within the artificial ventilation shown in FIG. 10 by controlling the PIP and the PEEP accordingly.

FIG. 11 shows the measurements of $paO_2$, $paCO_2$, and pHa (arterial pH) during the kinetic rotation therapy. As it can be seen, $paO_2$ improves continuously during the kinetic rotation therapy. The rotation period was switched during kinetic rotation therapy from 8 to 16 rotation periods per hour. Having a mean ventilation frequency of 10 to 40 breaths per minute, this results in 50 to 250 breaths per rotation period.

The schematic drawing of FIG. 11 is derived from an original on-line blood gas registration by the blood gas analyzer Paratrend (Diametrics, High Newcombe, UK) of a patient suffering from ARDS who is treated in a bed employing a Servo 300 ventilator (Siemens Elema, Solna, Sweden). Rotation angles ranged from −62° to +62°. While the mean $paO_2$ improves continuously during the kinetic rotation therapy, $paO_2$ also oscillates around a mean value resulting from turning the patient from one side to the other. The oscillation reflects the fact that artificially ventilating the patient at one side seems to be more effective for improving $paO_2$ than artificially ventilating the patient at the other side.

Without additional data the blood gas analysis does not give any information about the relationship between the rotation angle, the ventilator settings and their final effect on gas exchange. The registration shows, however, the influence of the rotation period on the mean $paO_2$ and its oscillations. As stated above, in this particular example the rotation period was switched from 8 to 16 rotation periods per hour. While $paO_2$ increased, the amplitude of the oscillations was considerably reduced, indicating that the individual and time dependent influences of the sick lung and the normal lung are minimized.

FIG. 12 shows a measurement of the compliance during the kinetic rotation therapy. As expected, the compliance improves during the kinetic rotation therapy. As explained above, the ventilation parameters are adapted accordingly. It should be noted, that the range of the rotation angle shown in FIG. 12 represents only one example. Higher values for the rotation angle, i.e., ±90° or even more, can be chosen if required.

The compliance is displayed as a function of the rotation angle. When the patient is turned towards +62° rotation angle (following the bold line from its beginning at 0° rotation angle) the compliance decreases to almost half of its initial value at 0° rotation angle. As the patient is turned back to the initial position at 0° rotation angle, the compliance increases even beyond the initial value and continues to improve as the patient is turned towards negative rotation angles. The compliance reaches its temporary maximum at −62° rotation angle. As the patient is turned back to the initial position at 0° rotation angle, the compliance decreases continuously but remains significantly above the value at the previous zero-degree transition. As kinetic rotation therapy continues, the compliance values follow a similar pattern as described; however, the incremental improvements per rotation cycle become smaller, and it is apparent that a certain saturation of the therapeutic effect has been reached. For the sake of an even further improvement of the lung function, a superimposed active therapeutic intervention like an alveolar recruitment maneuver by means of a ventilator should be applied.

FIG. 13 shows a schematic diagram of one exemplary embodiment of a method for controlling the positioning of a patient in or on a patient support surface. In this exemplary embodiment, an artificial ventilator (not shown) is used to artificially ventilate the lung of a patient 601. The status of the artificially ventilated lung is determined by measuring one or more physiological parameters such as ventilation status measures 603. In a therapy optimization step 605, one or more of the ventilation status measures 603 is used to generate feedback that can then be used for controlling at least one ventilation parameter 607 of the artificial ventilator and/or the automated positioning 609 or manual positioning 611 of the patient 601.

With regard to specific optimization methods, European patent application EP04007580.6 discloses that the ventilation status information and the rotation status information can be used to optimize each other, but it does not disclose specifically how. Methods for optimization can be derived from optimization methods known in the systems engineering and process control arts. Essentially, a "cost function" can be computed and then the minimum of that cost function determined. For example, various parameters can be measured relating to a patient's position and ventilator settings. In addition, physiological parameters can also be recorded. In certain exemplary embodiments, physiological parameters that are direct measurements may be combined to yield a more comprehensive quantification of lung performance. Data may then be taken to establish how the parameters are related to each other, and a cost function may then be developed based on specific desired outputs. The minimum of the cost function may then be used as a point to determine the optimum values for the various parameters which can be controlled. A control system may automatically adjust these parameters to approximately their optimum levels, or a caregiver may manually adjust the parameters to such levels. In certain exemplary embodiments, an indicator (such as a visual or audible signal) can alert a caregiver when the optimum level of a parameter (or parameters) has been reached.

Alternatively, a "benefit function" can also be defined and a maximum sought. In the ventilation and rotation optimization case, an example of one such cost function is lung stiffness measured at the airway. Several paired measures of stiffness and rotation position can be obtained, and then either the rotation position with lowest stiffness can be chosen or a smooth function (linear or curved) can be fit between the points and the minimum of the fitted function determined by typical methods. Note that any rotation parameter or ventilation parameter could be substituted in the above scheme for "rotation position," while any physiologic status parameter could be substituted for "lung stiffness." Other systems may include position parameters measuring the pitch of the patient (i.e. the relative elevation of the patient's head to the patient's feet.)

In fact, multiparameter optimizations can be performed the same way. Using multiple measures of physiologic status, an N-dimensional cost function can be constructed and its minimum found. Even more complex combinations are possible, where multiple physiologic status measures are used as inputs and multiple controlled parameters, such as ventilation and rotation parameters, determined as an M-dimensional measure of cost-benefit is developed. This is generally known as multivariate optimal control and is the best method for obtaining maximum benefit from both therapies simultaneously. For example, lung stiffness, oxygen consumption, ETCO2 and upper inflection point pressure can all be measured at several settings of rotation position, rotation rate, and ventilation drive parameters (Vtidal, PIP, PEEP, etc.) with a N×M cost function developed. The minimum cost function value can be determined from the data points and a minimum found.

In order to prevent or assist with the treatment of ventilator-associated pneumonia, as well as aspiration pneumonia due to aspiration and subsequent aspiration of gastric contents, certain exemplary embodiments of the present invention comprise controlling the pitch of the patient's position, either through automated control or manual control, based on feedback obtained through the measurement of various ventilation status measures.

* * * * *

It should be understood that the present apparatuses and methods are not intended to be limited to the particular forms disclosed. Rather, they are to cover all modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

We claim:

1. A method of optimizing ventilation parameters for a patient, the method comprising:
   (a) using an artificial ventilator to artificially ventilate a lung of a patient;
   (b) setting a first ventilation parameter at an initial value;
   (c) placing the patient in a first position;
   (d) obtaining a first value of a first physiological parameter when the first ventilation parameter is at the initial value and the patient is in the first position;
   (e) varying the first ventilation parameter to a subsequent value;
   (f) obtaining a second value of the first physiological parameter when the first ventilation parameter is at the subsequent value;
   (g) placing the patient in a second position;
   (h) obtaining a third value of the first physiological parameter when the patient is in the second position; and
   (i) calculating a minimum value of a cost function to determine an optimum value for the first ventilation parameter and for the position of the patient, wherein the cost function is calculated using the initial and subsequent values of the first ventilation parameter, the first and second positions of the patient, and the first, second and third values of the first physiological parameter.

2. The method of claim 1, further comprising:
   (a) obtaining a first value of a second physiological parameter when the first ventilation parameter is at the initial value and the patient is in the first position;
   (b) obtaining a second value of the second physiological parameter when the first ventilation parameter is at the subsequent value;
   (c) obtaining a third value of the second physiological parameter when the patient is in the second position;
   (d) calculating a minimum value of the cost function to determine an optimum value for the first ventilation parameter and for the position of the patient, wherein the cost function is calculated using the initial and subsequent values of the first ventilation parameter, the first and second positions of the patient, and the first, second and third values of the first and second physiological parameters.

3. The method of claim 2, wherein the first and second physiological parameters comprise measurements of the patient's lung mechanics and series dead space.

4. The method of claim 2, wherein the first and second physiological parameters are direct measurements that may be combined to yield a more comprehensive quantification of lung performance as compared to a quantification of lung performance based on a single physiological parameter.

5. The method of claim 1 wherein the first position is a different pitch than the second position.

6. The method of claim 1 wherein placing the patient in a second position comprises raising or lowering the head-end of the patient with respect to the foot-end of the patient.

7. The method of claim 1 wherein the first position is a different rotational position than the second position.

8. The method of claim 1 wherein placing the patient in a second position comprises rotating a support surface about its longitudinal axis.

9. The method of claim 1 wherein placing the patient in a second position comprises adjusting an adjustable air cushion supporting the patient.

10. The method of claim 1, further comprising a control system to automatically adjust the first ventilation parameter and a position of the patient to approximately the optimum values of the first ventilation parameter and the position of the patient.

11. The method of claim 1 wherein the first ventilation parameter and a position of the patient are manually adjusted by a caregiver to be set at approximately the optimum values.

12. The method of claim 1, further comprising an indicator to indicate when the first ventilation parameter and a position of the patient are at approximately the optimum values.

13. The method of claim 1 wherein the first physiological parameter comprises a respiratory parameter.

14. The method of claim 1 wherein the first physiological parameter comprises one of direct $VO_2$, $paO_2$, and pulmonary mechanics measurements.

15. The method of claim 1 wherein the first physiological parameter comprises one or more of upper and lower inflection points of the expiratory and inspiratory pressure-volume curves and the airway pressure at the point of maximal pressure-volume compliance (Pmax).

16. The method of claim 1, wherein the first physiological parameter comprises a hemodynamic parameter.

17. The method of claim 1, wherein the first physiological parameter comprises one or more of $DO_2$, indirect $VO_2$, $SpO_2$, invasive cardiac output, cardiac stroke work, stroke volume, right heart end diastolic volumes, pulmonary vascular resistance, pulmonary capillary pressures, pulmonary vascular compliance, $O_2$ extraction ratio, Qs/Qt shunt fraction, and extravascular lung water measurements.

18. The method of claim 1, wherein the first physiological parameter comprises imaging data.

19. The method of claim 18, wherein the imaging data comprises one or more of electrical impedence tomography (EIT) data and computed tomography (CT) data.

20. The method of claim 1, wherein the cost function is defined using one or more of the following measurements: the air viscosity factor of the patient's lungs, the barometric pressure, the lung elastance factor of the patient, the measured levels of carbon dioxide and oxygen of the patient, and the metabolic rate ratio of the patient.

21. A system for optimizing treatment for a patient, the system comprising:
   a support surface configured for placement in a first position and a second position;
   an artificial ventilator configured to artificially ventilate a lung of the patient;
   measuring equipment configured to obtain values for one or more physiological parameters, ventilation parameters, and position parameters;
   a feedback system configured to send the values for the one or more physiological parameters, ventilation parameters, and position parameters to an analysis system, wherein the analysis system is configured to calculate a cost function using the values for the one or more physiological parameters, ventilation parameters, and position parameters; and
   a control system configured to adjust the one or more ventilation parameters and position parameters to minimize the cost function.

22. The system of claim 21 wherein the support surface is rotatable about its longitudinal axis.

23. The system of claim 21 wherein the support surface comprises adjustable air bladders.

24. The system of claim 21 wherein the control system automatically adjusts the one or more ventilation parameters and the position parameters to minimize the cost function.

25. The system of claim 21 wherein the control system comprises manual adjustments by a caregiver and an audible or visible indicator that indicates when the one or more ventilation parameters and position parameters are adjusted so that the cost function is minimized.

26. The system of claim 21 wherein the support surface is configured to adjust the pitch of the patient.

27. A method of optimizing the treatment of a patient, the method comprising:
   using an artificial ventilator to artificially ventilate a lung of the patient;
   measuring a physiological parameter;
   measuring the ventilation parameter;
   defining a cost function calculated using the physiological parameter, the ventilation parameter and the pitch of the patient;
   determining a minimum value of the cost function; and
   adjusting the ventilation parameter and the pitch of the patient to minimize the value of the cost function.

* * * * *

UNITED STATES PATENT AND TRADEMARK OFFICE
CERTIFICATE OF CORRECTION

PATENT NO. : 8,202,226 B2  Page 1 of 1
APPLICATION NO. : 12/016030
DATED : June 19, 2012
INVENTOR(S) : George Hutchinson et al.

It is certified that error appears in the above-identified patent and that said Letters Patent is hereby corrected as shown below:

In title page, item (56) References Cited - U.S. PATENT DOCUMENTS, insert
--7,137,160 B2  11/2006  Hand et al.--

Signed and Sealed this
Fourteenth Day of August, 2012

David J. Kappos
*Director of the United States Patent and Trademark Office*